(12) United States Patent
Sugise et al.

(10) Patent No.: US 6,388,140 B2
(45) Date of Patent: May 14, 2002

(54) METHOD AND PRODUCING CYCLODODECANONE COMPOUND

(75) Inventors: Ryoji Sugise; Shuji Tanaka; Kohichi Kashiwagi; Takashi Doi; Masayuki Nishio; Sadao Niida; Tsunao Matsuura, all of Ube (JP)

(73) Assignee: Ube Industries, Ltd., Ube (JP)

( * ) Notice: Subject to any disclaimer, the term of this patent is extended or adjusted under 35 U.S.C. 154(b) by 0 days.

(21) Appl. No.: 09/783,921

(22) Filed: Feb. 15, 2001

(30) Foreign Application Priority Data

Feb. 18, 2000 (JP) ........................ 2000-040632

(51) Int. Cl.$^7$ .............................................. C07C 45/00
(52) U.S. Cl. ..................................................... 568/341
(58) Field of Search ................................. 568/341, 361

(56) References Cited

U.S. PATENT DOCUMENTS

| | | | | |
|---|---|---|---|---|
| 3,855,303 A | * | 12/1974 | Bishop | ........................ 568/341 |
| 4,734,529 A | * | 3/1988 | Berg et al. | ................... 568/341 |
| 4,885,397 A | * | 12/1989 | Bueschken | ................... 568/341 |
| 4,980,511 A | * | 12/1990 | Hoelderich et al. | ......... 568/341 |

FOREIGN PATENT DOCUMENTS

| | | |
|---|---|---|
| DE | 36 01 380 | 7/1987 |
| DE | 37 44 094 | 7/1989 |
| DE | DE 40 18 262 A | 12/1991 |
| SU | 407 874 | 11/1973 |

OTHER PUBLICATIONS

A. N. Nesmeyanovc Institute of Heteroorganic Compounds, Acad. of Sci. of the USSR; Zhurnal Organicheskoi Khimii, vol. 26, No. 7, pp. 1497–1500 (Jul. 1990).
Journal of Molecular Catalysis, 73 (1992) 157–166 (1992).
L. I. Zakharkin, et al., "Isomerization of trans–1,2–epoxy–cis,trans–5,9–cyclododecadiene, trans–1,2–epoxy–trans, trans–5,9–cyclododecadiene, and trans–epoxycyclododecane to the corresponding ketones under the action of lithium and magnesium bromides and iodides" J. Org. Chem., USSR, 26, 1291–94 (1990).

* cited by examiner

Primary Examiner—Alan Siegel
(74) Attorney, Agent, or Firm—Morgan, Lewis & Bockius LLP

(57) ABSTRACT

A cyclododecanone compound is produced in a high reaction rate, with a high conversion of the starting compound, and with a high selectivity to and a high yield of the target compound by isomerizing an epoxycyclododecane compound in the presence of a catalyst comprising lithium bromide and/or lithium iodide, without using a solvent or in a non-polar solvent, in an inert gas atmosphere, while substantially no polymeric compounds having a high boiling temperature is produced.

8 Claims, No Drawings

METHOD AND PRODUCING CYCLODODECANONE COMPOUND

BACKGROUND OF THE INVENTION

1. Field of the Invention

The present invention relates to a method of producing a cyclododecanone compound. More particularly, the present invention relates to a method of producing a cyclododecanone compound by an isomerization of the corresponding epoxycyclododecane compound in the presence of a catalyst comprising lithium bromide and/or lithium iodide in an inert gas atmosphere. Cyclododecanone compounds are useful as materials for producing laurolactum, dodecanedioic acids, dodecane diols and perfumes.

2. Description of the Related Art

A plurality of reports on methods of producing cyclododecanone compounds by isomerization of epoxycyclododecane compounds in the presence of a catalyst comprising an alkali metal halide have been published.

For example, German Patent (DE) No. 3,601,380 discloses a method in which cyclodeca-3,7-diene-1-one is produced in a yield of 98.7% by an isomerization reaction of 1,2-epoxycyclododeca-5,9-diene in the presence of sodium iodide catalyst in a reaction medium consisting of polyethyleneglycol. Also, German Patent (DE) No. 3,744,094 discloses a method in which cyclododecanone is produced in a yield of 94% by an isomerization reaction of an epoxycyclododecane in the presence of a lithium chloride catalyst in a reaction medium consisting of N-methylpyrrolidone and/or N,N'-dimethylethyleneurea.

The prior methods mentioned above are disadvantageous in that since a polar solvent such as polyethyleneglycol or N,N'-dimethylethyleneurea is employed, the recovery and decomposition of the solvent may cause the cost of the reaction to increase, and the reaction apparatus is required to have a high pressure resistant. Further, a dilution effect and a salvation effect of the polar solvent on the reaction system cause the reaction rate to decrease and the scale of the reaction apparatus to be large.

Soviet Union (SU) Patent No. 407,874 discloses an isomerization reaction of an epoxycyclododecane compound in the presence of anhydrous LiBr without using a solvent. In examples disclosed in the SU patent, it is reported that when the isomerization was carried out at a reaction temperature of 120 to 130° C. for 18 hours or at a temperature of 200° C. for 3 hours, the target cyclododecanone was obtained in a yield of about 100% in the former or 83.3% in the latter. In the former case, the reaction time was too long and thus the reaction conditions may not be practical. Also, in the latter case, a by-product having a high boiling temperature was produced and a discoloration of the reaction liquid was found. When the catalyst is recycled and repeatedly used, the high boiling temperature product accumulated in the reaction system causes the reaction to be affected and a specific procedure for removing the high boiling temperature product to be necessary.

It is assumed that the reaction rate can be increased by increasing the concentration of the catalyst in the reaction system. In the reaction system disclosed in the above-mentioned SU patent, the concentration of the LiBr dissolved in the reaction system was saturated, and thus a further increase in the LiBr concentration was impossible. When the reaction temperature is increased to increase the reaction rate, undesirable side reactions occur, the yield of the target product decreases, high boiling temperature substances are produced and the reaction system is discolored.

Further, Zh. Org. Khim (1990), 26(7), 1497–1500 reports that when an isomerization of epoxycyclododecane was carried out at a temperature of 150° C. for 10 hours in the presence of a catalyst comprising lithium bromide without using a solvent, a target cyclodedecanone was produced in a yield of 96.6%, and when the same isomerization as above was carried out except that the catalyst comprised lithium iodide, and the reaction temperature and time were 150° C. and 5 hours, the target cyclodedecanone was obtained in a yield of 91.2%. However, the report is quite silent as to the reaction atmospheric gas. In the method of the report, to increase the conversion of the starting compound to the target compound to about 100%, a long reaction time is necessary, and the long reaction time causes high boiling temperature substances to be produced.

In the case where a cyclododecanone compound is industrially produced by an isomerization of an epoxycyclododecanone compound, since the boiling temperature of the starting epoxycyclododecane compound is approximately equal to that of the target cyclodedecanone compound, usually the separation of the starting compound from the target product by distillation is extremely difficult. Thus, in order to produce the cyclododecanone compound in a high degree of purity, it is necessary to control the conversion of the epoxycyclododecane compound to approximately 100%. For this, it is absolutely necessary to increase the isomeization reaction rate. To increase the reaction rate, an increase in the reaction temperature may be tried and/or an increase in the content of the catalyst in the reaction system may be attempted.

However, as mentioned above, the increase in the reaction temperature causes undesirable side reactions to occur, high boiling temperature substances to be produced, the yield of the target cyclododecanone compound to decrease.

On other hand, to increase the conversion of the starting epoxycyclododecane compound, it may be considered to further increase the concentration of the catalyst in the reaction system. However, the increase in the catalyst concentration is not practical in consideration of the solubility of the catalyst in the reaction system and the increase in production cost of the target product due to the increase in the amount of the catalyst.

As mentioned above, the conventional methods of producing the cyclododecanone compounds by the isomerization of epoxycyclododecane compounds are unsatisfactory due to a low reaction rate, a low conversion of the starting compound, a low selectivity of the target compound, production of undesirable high boiling temperature substance, and a low efficiency.

Therefore, a new method enabling the industrial production of the target cyclododecanone compound at a high reaction rate, with a high conversion of the starting compound, with a high selectivity to the target compound and with a high efficiency, while the side reaction for the production of undesired high boiling temperature substances is controlled, is strongly demanded.

SUMMARY OF THE INVENTION

An object of the present invention is to provide a method of producing a cyclododecanone compound by isomerization of an epoxycyclododecane compound at a high reaction rate at a high conversion at a high selectivity, with a high industrial efficiency, while substantially preventing the production of high boiling temperature substances.

The inventors of the present invention made an extensive study of means for attaining the above-mentioned object, and found that when the isomerization of an epoxycyclododecane compound is carried out in the presence of lithium bromide and/or lithium iodide in an inert gas atmosphere, the target cyclododecanone compound can be produced at an enhanced reaction rate, and all the above-mentioned problems of the prior acts can be solved. The present invention has been completed on the basis of the above-mentioned finding.

The method of the present invention for producing a cyclododecanone compound comprises isomerizing an epoxycyclododecane compound in the presence of a catalyst comprising at least one member selected from the group consisting of lithium bromide and lithium iodide, without using a solvent or in a non-polar solvent, in an inert gas atmosphere.

In the method of the present invention for producing a cyclododecanone compound, the epoxycyclododecane compound is preferably selected from the group consisting of saturated and unsaturated monoepoxy-cycloaliphatic compounds having a cyclic structure formed from 12 carbon atoms and an epoxy structure formed from one oxygen atom and two carbon atoms of the 12 carbon atoms being adjacent to each other and bonded to the oxygen atom.

In the method of the present invention for producing a cyclododecanone compound, the epoxycyclododecane compound is also preferably selected from the group consisting of epoxycyclododecane, epoxycyclododecenes, epoxycyclododecadienes, and epoxycyclododecatrienes.

In the method of the present invention for producing a cyclododecanone compound, the cyclododecanone compound is preferably selected from the group consisting of saturated and unsaturated cycloaliphatic compounds having a cyclic structure formed from 12 carbon atoms and a carbonyl structure formed from an oxygen atom and one of the 12 carbon atoms bonded to the oxygen atom through a double bond.

In the method of the present invention for producing a cyclododecanone compound, the cyclododecanone compound is also preferably selected from the group consisting of cyclododecanone, cyclododecenones, cyclododecadienones and cyclododecatrienones.

In the method of the present invention for producing a cyclododecanone compound, the catalyst is preferably The present in an amount of 0.0001 to 0.1 mole per mole of the epoxycyclododecane compound.

In the method of the present invention for producing a cyclododecanone compound, the isomerizing reaction for the epoxycyclododecane compound is preferably carried out at a temperature of 100° C. to 300° C.

In the method of the present invention for producing a cyclododecanone compound, the inert gas preferably comprises at least one member selected from the group consisting of helium, neon, argon, krypton, xenon, hydrogen, nitrogen, carbon monoxide, carbon dioxide, methane, and ethylene gases.

DESCRIPTION OF THE PREFERRED EMBODIMENTS

The epoxycyclododecane compound usable as a starting compound for the method of the present invention is selected from the group consisting of saturated and unsaturated monoepoxy-cycloaliphatic compounds having a cyclic structure formed from 12 carbon atoms and an epoxy structure formed from one oxygen atom and two carbon atoms of the above-mentioned 12 carbon atoms being adjacent to each other and bonded to the oxygen atom.

The $C_{12}$ cyclic structure of the epoxycyclododecane compound may be saturated or may have one or more double bonds.

Particularly, the epoxycyclododecane compound is preferably selected from, for example, epoxycyclododecane, epoxycyclododecenes, epoxycyclododecadienes and epoxycyclododecatrienes, more preferably epoxycyclododecane and epoxycyclododecadienes. The epoxycyclododecane compounds having one or more double bonds include various isomers. Even in this case, there is no limitation to the locations of the double bonds and the epoxy structure as defined above, in relationship to each other, and the unsaturated epoxycyclododecane compounds may be in a cis-form or in a trans-form with respect to the epoxy group and/or the double bond. The starting material for the method of the present invention may contain two or more types of epoxycyclododecane compounds different in chemical structure from each other.

The target cyclododecanone compound of the method of the present invention is a cyclododecanone compound corresponding to the starting epoxycyclododecane compound and selected from the group consisting of saturated and unsaturated cycloaliphatic compounds having a cyclic structure formed from 12 carbon atoms and a carbonyl structure formed from an oxygen atom and one of the above-mentioned 12 carbon atoms bonded to the oxygen atom through a double bond.

Particularly, the target cyclododecanone compound of the method of the present invention is preferably selected from the group consisting of cyclododecanone, cyclododecenones, cyclododecadienones and cyclododecatrienones.

The catalyst usable for the isomerization reaction of the method of the present invention comprises at least one member selected from lithium bromide and lithium iodide. When the catalyst is practically employed for the method of the present invention, no specific pre-treatment is necessary. The lithium bromide and iodide may be anhydrous or may be hydrated. Particularly, the catalyst comprises at least one member selected from anhydrous lithium bromide, lithium bromide monohydrate, lithium bromide dihydrate, lithium bromide trihydrate, anhydrous lithium iodide, lithium iodide monohydrate, lithium iodide dihydrate, and lithium iodide trihydrate. The catalyst may be supplied in the state of an aqueous solution to the reaction.

The amount of the catalyst to be used for the reaction of the method of the present invention is established in consideration of the reaction conditions. Usually, the catalyst is preferably employed in an amount of 0.0001 to 0.1 mole, more preferably 0.001 to 0.05 mole, per mole of the epoxycyclododecane compound. If the amount of the catalyst is too small, the reaction time necessary to complete the reaction may be too long and thus industrially unsatisfactory. If the catalyst amount is too large, the production cost may be too high and thus industrially unsatisfactory.

In the method of the present invention, it is important that the catalytic isomerization reaction of the epoxycyclododecane compound is carried out in an inert gas atmosphere. In the present invention, it was found for the first time that the inert gas atmosphere enables the catalytic isomerization of the epoxycyclododecane compound to industrially produce the target cyclododecanone compound with a high efficiency, at a high reaction rate, at a high conversion of the expoxycyclododecane compound, at a high selectivity to the target cyclododecanone compound, while the production of undesired by-product having a high boiling temperature is substantially prevented.

The inert gas usable for the method of the present invention preferably comprises at least one member selected from the group consisting of helium, neon, argon, krypton, xenon, hydrogen, nitrogen, carbon monoxide, carbon dioxide, methane, and ethylene gases, more preferably nitrogen, argon and carbon dioxide gases.

In the method of the present invention, the catalytic isomerization reaction is carried out without using a solvent or in a non-polar solvent. Usually, no solvent is employed. In this case, the epoxycyclododecane compound serves as a solvent for the reaction system. Namely, in this embodiment of the method of the present invention, a reaction mixture of an epoxycyclododecane compound with a catalyst is placed in a reactor, the reactor is filled with an inert gas, and the resultant reaction system is subjected to a catalytic isomerization reaction.

The reaction of the method of the present invention may be carried out in a non-polar solvent. The non-polar solvent may comprise at least one member selected from cyclic hydrocarbons having 6 to 12 carbon atoms. The non-polar solvent is usually employed in an amount in weight not more than that of the epoxycyclododecane compound.

The reaction temperature for the method of the present invention is preferably established within the range of from 100 to 300° C., in consideration of the composition of the catalyst. When lithium bromide is used as a catalyst, the reaction temperature is preferably in the range of from 120 to 300° C., more preferably from 150 to 280° C., still more preferably from 170 to 260° C. When lithium iodide is employed as a catalyst, the reaction temperature is preferably in the range of from 100 to 300° C, more preferably from 150 to 280° C., still more preferably 150 to 260° C. If the reaction temperature is too low, the reaction rate may be decreased, and the decrease in the reaction rate is industrially disadvantageous. If the reaction temperature is too high, the production of the high boiling temperature substance may be promoted.

The reaction time of the method of the present invention is variable in response to the composition and the amount of the catalyst and the reaction temperature. Usually, the reaction time is preferably not more than 10 hours.

There is no limitation to the type of the reaction system or apparatus. Namely, the isomerization reaction of the method of the present invention may be effected in a batch type reaction system or apparatus or a continuous type reaction system or apparatus. Also, there is no limitation to the reaction pressure. Namely, the reaction is usually carried out under an ambient atmospheric pressure and optionally under a reduced pressure or an increased pressure.

In the method of the present invention, since the conversion of the epoxycyclododecane compound can be controlled to approximately 100%, the target cyclododecanone compound can be isolated and refined by a usual distillation procedure, namely at a temperature of 80 to 280° C. under a pressure of 0.0001 to 0.1 MPa.

EXAMPLES

The present invention will be further illustrated by the following examples.

(1) In the examples and comparative examples, the quantitative analysis of the starting material and the resultant product was carried out by a gas chromatography using a capillary column in an internal standard method.

The conversion of the starting epoxycyclododecane compound is a percentage of the molar amount of consumed epoxycyclododecane compound based on the original molar amount of the compound; the selectivity to the resultant cyclododecanone compound is a percentage of the molar amount of the resultant cyclododecanone compound based on the molar amount of the consumed epoxycyclododecane compound, and the yield of cyclododecanone compound is a percentage of the molar amount of the resultant cyclododecanone compound based on the original molar amount of the epoxycyclododecane compound.

(2) The analysis of high boiling temperature substance was effected by using a gel permeation chromatography. The analysis results were indicated in area percentage (%).

Example 1

In a glove box filled with nitrogen gas, a glass flask having a capacity of 50 ml, equipped with a thermometer, a stirrer and a reflux condenser tube was charged with 4.56 g (25.0 millimoles) of epoxycyclododecane having a cis/trans form molar ratio of 66:34 which will be represented by ECD hereinafter, and 16.8 mg (0.13 millimoles) of a catalyst consisting of lithium iodide. The 50 ml flask containing the ECD and the catalyst was heated in an oil bath to a temperature of 200° C., and maintained at the above-mentioned temperature under the ambient atmospheric pressure for 4 hours, to isomerize the ECD. During the reaction procedure, the flask was sealed with an argon gas to prevent a penetration of air into the flask. After the reaction was completed, the resultant reaction liquid was cooled to room temperature, and a sample of the resultant solid reaction product was dissolved in toluene and subjected to the gas chromatographic analysis.

As results of the analysis, it was confirmed that the conversion of the epoxycyclododecane was 100%, the target cyclododecanone (which will be represented by CDON hereinafter) was obtained in an amount of 4.51 g (24.7 millimoles and in a yield of 99%. The resultant reaction liquid had a very light yellow color, and substantially no polymeric substance was found. The results are shown in Table 1.

Comparative Example 1

The same reaction procedures and analysis as in Example 1 were carried out with the following exceptions.

The charging procedure of the starting material and the catalyst was carried out in the ambient air atmosphere, and the reaction procedure was carried out without sealing the flask with the argon gas.

In the analysis results, the conversion of the ECD was 98%, and the CDON was produced in an amount of 4.18 g (22.9 millimoles in a yield of 92%. Also, it was confirmed that the resultant reaction liquid had a brownish black color, and thus polymeric substances were contained in the reaction liquid. The results are shown in Table 1.

Examples 2 and 3

In each of Examples 2 and 3, the same isomerization procedures and analysis as in Example 1 were carried out with the following exceptions.

The amount of the catalyst, the reaction temperature and the reaction time were changed to as shown in Table 1. Also, the analysis results are shown in Table 1.

Examples 4 to 6

In each of Examples 4 to 6, the same isomerization procedures and analysis as in Example 1 were carried out with the following exceptions.

As a catalyst, lithium bromide was employed in place of lithium iodide, and the amount of the catalyst, the reaction temperature and the reaction time were changed to as shown in Table 1. Also, the analysis results are shown in Table 1.

Comparative Examples 2 and 3

In each of Comparative Examples 2 and 3, the same isomerization procedures and analysis as in Comparative Example 1 were carried out with the following exceptions.

The amount of the catalyst, the reaction temperature and the reaction time were changed to as shown in Table 1. The analysis results are shown in Table 1.

Comparative Examples 4 to 6

In each of Comparative Examples 4 to 6, the same isomerization procedures and analysis as in Comparative Example 1 were carried out with the following exceptions.

In the catalyst, the lithium iodide was replaced by lithium bromide, and the amount of the catalyst, the reaction temperature and the reaction time were changed to as shown in Table 1. The results are shown in Table 1.

flask. After the reaction was completed, the resultant reaction liquid was cooled to room temperature, and a sample of the resultant solid reaction product was dissolved in toluene and subjected to the gas chromatographic analysis.

As results of the analysis, it was confirmed that the conversion of the 1,2-epoxycyclododeca-5,9-diene was 100%, the target cyclododeca-3,7-diene-1-one (which will be represented by CDEON hereinafter) was obtained in an amount of 4.47 g (24.4 millimoles and in a yield of 98%. The resultant reaction liquid had a very light yellow color, and substantially no polymeric substance was found. The results are shown in Table 2.

Example 8

The same isomerization procedures and analysis as in Example 7 were carried out with the following exceptions.

The amount of the catalyst, the reaction temperature and the reaction time were changed to as shown in Table 2.

The results are shown in Table 2.

Comparative Example 7

The same isomerization procedures and analysis as in Example 7 were carried out with the following exceptions.

TABLE 1

| Item Example No. | ECD (m mole) | Catalyst Compound and amount (mol %) | Reaction Temperature and time (° C/hr) | Reaction atmosphere | Conversion of ECD (%) | Selectivity to CDON (%) | Yield of CDON (%) | High boiling temperature substance (area %) | Discoloration |
|---|---|---|---|---|---|---|---|---|---|
| Example 1 | 25 | LiI (0.5) | 200/4 | N₂ + Ar | 100 | 99 | 99 | 0.62 | Light yellow |
| Comparative Example 1 | 25 | LiI (0.5) | 200/4 | Air | 98 | 94 | 92 | 8.63 | Brownish black |
| Example 2 | 25 | LiI (0.1) | 260/2 | N₂ + Ar | 100 | 94 | 94 | 1.15 | Light yellow |
| Comparative Example 2 | 25 | LiI (0.1) | 260/2 | Air | 100 | 93 | 93 | 4.66 | Brownish black |
| Example 3 | 25 | LiI (1.5) | 150/2 | N₂ + Ar | 97 | 97 | 95 | 0.41 | Light yellow |
| Comparative Example 3 | 25 | LiI (1.5) | 150/2 | Air | 91 | 91 | 83 | 2.39 | Brownish black |
| Example 4 | 25 | LiBr (3.0) | 260/5 | N₂ + Ar | 100 | 94 | 94 | 0.95 | Light yellow |
| Comparative Example 4 | 25 | LiBr (3.0) | 200/5 | Air | 100 | 84 | 84 | 1.62 | Brownish black |
| Example 5 | 25 | LiBr (3.0) | 260/4 | N₂ + Ar | 100 | 90 | 90 | 10.3 | Light yellow |
| Comparative Example 5 | 25 | LiBr (3.0) | 260/4 | Air | 100 | 83 | 83 | 22.4 | Brownish black |
| Example 6 | 25 | LiBr (3.0) | 150/10 | N₂ + Ar | 80 | 98 | 78 | 0.64 | Light yellow |
| Comparative Example 6 | 25 | LiBr (3.0) | 150/10 | Air | 37 | 71 | 26 | 8.12 | Brownish black |

Example 7

In a glove box filled with a nitrogen gas, a glass flask having a capacity of 50 ml, equipped with a thermometer, a stirrer and a reflux condenser tube was charged with 4.46 g (25.0 millimoles) of 1,2-epoxycyclododeca-5,9-diene which will be represented by ECDEN hereinafter, and 33.5 mg (0.25 millimoles) of a catalyst consisting of lithium iodide. The 50 ml flask containing the ECDEN and the catalyst was heated in an oil bath to a temperature of 200° C., and maintained at the above-mentioned temperature under the ambient atmospheric pressure for 2 hours, to isomerize the ECDEN. During the reaction procedure, the flask was sealed with an argon gas to prevent a penetration of air into the The charging procedure of the starting material and the catalyst was carried out in the ambient air atmosphere, and the reaction procedure was carried out without sealing the flask with the argon gas.

In the analysis results, the conversion of the ECDEN was 100%, and the CDEON was produced in an amount of 4.34 g (23.8 millimoles in a yield of 94%. Also, it was confirmed that the resultant reaction liquid had a black color, and thus polymeric substances were contained in the reaction liquid. The results are shown in Table 2.

Comparative Example 8

The same isomerization procedures and analysis as in Example 7 were carried out with the following exceptions.

The amount of the catalyst, the reaction temperature and the reaction time were changed to as shown in Table 2.

The results are shown in Table 2.

In the results, the conversion of ECD was 91%, the selectivity to CDON was 96%, the yield of CDON was 88%, and the reaction rate constant K was 1.7 (1/min·mole).

TABLE 2

| Item Example No. | ECD (m mole) | Catalyst Compound and amount (mol %) | Reaction Temperature and time (° C/hr) | Reaction atmosphere | Conversion of ECD (%) | Selectivity to CDON (%) | Yield of CDON (%) | High boiling temperature substance (area %) | Discoloration |
|---|---|---|---|---|---|---|---|---|---|
| Example 7 | 25 | LiI (1.0) | 200/2 | N₂ + Ar | 100 | 98 | 98 | 0.84 | Light yellow |
| Comparative Example 7 | 25 | LiI (1.0) | 200/2 | Air | 100 | 94 | 94 | 2.07 | Black |
| Example 8 | 25 | LiI (0.5) | 260/2 | N₂ + Ar | 100 | 94 | 94 | 0 | Light yellow |
| Comparative Example 8 | 25 | LiI (0.5) | 260/2 | Air | 100 | 82 | 82 | 8.44 | Black |

Example 9

In a glove box filled with a nitrogen gas, a glass flask having a capacity of 50 ml, equipped with a thermometer, a stirrer and a reflux condenser tube was charged with 4.56 g (25.0 millimoles) of epoxycyclododecane (ECD) having a cis/trans form molar ratio of 66:34, and 16.5 mg (0.13 millimoles: 0.023 millimoles/l) of a catalyst consisting of lithium iodide. The 50 ml flask containing the ECD and the catalyst was heated in an oil bath to a temperature of 200° C., and maintained at the above-mentioned temperature under the ambient atmospheric pressure for 2 hours, to isomerize the ECD. During the reaction procedure, the flask was sealed with an argon gas to prevent a penetration of air into the flask. After the reaction was completed, the resultant reaction liquid was cooled to room temperature, and a sample of the resultant solid reaction product was dissolved in toluene and subjected to the gas chromatographic analysis.

As results of the analysis, it was confirmed that the conversion of the ECD was 95%, the target cyclododecanone (CDON) was obtained in a selectivity of 99% and in a yield of 94%.

Measurement of reaction rate constant K

The same reaction as mentioned above was carried out except that the ECD and the catalyst were employed in amounts of twice the above-mentioned amounts. During the reaction procedure, at each of stages of 5 minutes, 10 minutes, 20 minutes and 30 minutes after the start of the reaction, a sample in an amount of about 0.4 g of the reaction liquid was taken and subjected to an analysis.

The reaction rate constant K of the reaction was calculated in accordance with the following reaction rate equation:

$$[CDON]/dt = K[ECD]$$

wherein [CDON] represents a concentration of CDON, [ECD] represents a concentration of ECD.

In a result of the calculation, K=2.0 (1/min·mole).

The results are shown in Table 3.

Comparative Example 9

The same reaction procedures and analysis as in Example 9 were carried out except that the reaction was carried out in the ambient air atmosphere.

The results are shown in Table 3.

Comparative Example 10

In a glove box filled with a nitrogen gas, a glass flask having a capacity of 50 ml, equipped with a thermometer, a stirrer and a reflux condenser tube was charged with 6.96 g (38.2 millimoles) of epoxycyclododecane (ECD) having a cis/trans form molar ratio of 66:34, 2.21 g of polyethyleneglycol (PEG) having an average molecular weight of 400, and 30.0 mg (0.22 millimoles: 0.023 mole/l) of a catalyst consisting of lithium iodide. The 50 ml flask containing the ECD, PEG and the catalyst was heated in an oil bath to a temperature of 200° C., and maintained at the above-mentioned temperature under the ambient atmospheric pressure for 2 hours, to isomerize the ECD. During the reaction procedure, the flask was sealed with an argon gas to prevent penetration of air into the flask. After the reaction was completed, the resultant reaction liquid was cooled to room temperature, and a sample of the resultant reaction liquid was dissolved in toluene and subjected to the same gas chromatographic analysis as in Example 1.

As results of the analysis, it was confirmed that the conversion of the ECD was 58%, the selectivity to the target CDON was 96% and the yield of the CDON was 55%.

Measurement of reaction rate constant K

The same reaction as mentioned above was carried out except that the ECD and the catalyst were employed in amounts of twice the above-mentioned amounts. During the reaction procedure, at each of stages of 5 minutes, 10 minutes, 20 minutes and 30 minutes and 45 minutes after the start of the reaction, a sample in an amount of about 0.4 g of the reaction liquid was taken and subjected to the analysis.

The reaction rate constant K calculated from the analysts results was 0.36 (1/min·mole).

The analysis results are shown in Table 3.

Comparative Example 11

In a glove box filled with a nitrogen gas, a glass flask having a capacity of 50 ml, equipped with a thermometer, a stirrer and a reflux condenser tube was charged with 6.96 g (38.2 millimoles) of epoxycyclododecane (ECD) having a cis/trans form molar ratio of 66:34, 2.16 g of N,N'-dimethylethyleneurea (DMI), and 33.1 mg (0.25 millimoles:

0.023 mole/l) of a catalyst consisting of lithium iodide. The 50 ml flask containing the ECD, DMI and the catalyst was heated in an oil bath to a temperature of 200° C., and maintained at the above-mentioned temperature under the ambient atmospheric pressure for 2 hours, to isomerize the ECD. During the reaction procedure, the flask was sealed with an argon gas to prevent penetration of air into the flask. After the reaction was completed, the resultant reaction liquid was cooled to room temperature, and a sample of the resultant reaction liquid was dissolved in toluene and subjected to the same gas chromatographic analysis as in Example 1.

As results of the analysis, it was confirmed that the conversion of the ECD was 45%, the selectivity of the target CDON was 90% and the yield of the CDON was 41%.

Measurement of reaction rate constant K

The same reaction as mentioned above was carried out except that the ECD and the catalyst were employed in amounts of twice the above-mentioned amounts. During the reaction procedure, at each of stages of 5 minutes, 10 minutes, 20 minutes and 30 minutes and 45 minutes after the start of the reaction, a sample in an amount of about 0.4 g of the reaction liquid was taken and subjected to the analysis.

The reaction rate constant K calculated from the analysts results was 0.21 (1/min·mole).

The results are shown in Table 3.

As results of the analysis, it was confirmed that the cyclododecanone was recovered in an amount of 99%.

Namely, it was confirmed that almost all of the cyclododecanone could be recovered. The resultant liquid had a deep black color.

The method of the present invention enables a cyclododecanone compound to be industrially produced by an isomerization reaction of an epoxycyclododecane compound at a high reaction rate, with a high conversion, of the epoxycyclododecane compound, with a high selectivity to the cyclododecanone compound, in a high yield of the cyclododecanone and in a substantially no yield of high boiling temperature substance.

What is claimed is:

1. A method of producing a cyclododecanone compound comprising
    isomerizing an epoxycyclododecane compound in the presence of a catalyst comprising at least one member selected from the group consisting of lithium bromide and lithium iodide, without using a solvent or in a non-polar solvent, in an inert gas atmosphere.

2. The method of producing a cyclododecanone compound as claimed in claim 1, wherein the epoxycyclododecane compound is selected from the group consisting of saturated and unsaturated monoepoxy-cycloaliphatic compounds having a cyclic structure formed from 12 carbon atoms and an epoxy structure formed from one oxygen atom

TABLE 3

| Item Example No. | ECD (mol/l) | Catalyst Compound and amount (mol/l) | Solvent | Reaction Temperature and time (° C./hr) | Reaction atmosphere | Conversion of ECD (%) | Selectivity of CDON (%) | Yield of CDON (%) | Reaction rate constant (1/min · mol) |
|---|---|---|---|---|---|---|---|---|---|
| Example 9 | 4.45 | LiI (0.023) | None | 200/2 | $N_2$ + Ar | 95 | 99 | 94 | 2.0 |
| Comparative Example 9 | 4.45 | LiI (0.023) | None | 200/2 | Air | 91 | 96 | 88 | 1.7 |
| 10 | 3.56 | LiI (0.023) | PEG 21 vol % | 200/2 | $N_2$ + Ar | 58 | 96 | 55 | 0.36 |
| 11 | 3.50 | LiI (0.023) | DMI 22 vol % | 200/2 | $N_2$ + Ar | 45 | 90 | 41 | 0.21 |

Note:
The reaction rate constant K was determined in accordance with the equation: $[CDON]/dt = K[ECD]$
When no solvent was used, the K was a value of the reaction up to 30 minutes after the start of the reaction, and when a solvent was employed, the K was a value of the reaction up to 45 minutes after the start of the reaction.

Comparative Example 12

In the ambient air atmosphere, a glass flask having a capacity of 50 ml, equipped with a thermometer, a stirrer and a reflux condenser tube was charged with 4.56 g (25.0 millimoles) of cyclododecanone, and 33.5 mg (0.25 millimoles) of a catalyst consisting of lithium iodide. The 50 ml flask containing the CDON and the catalyst was heated in an oil bath to a temperature of 200° C., and maintained at the above-mentioned temperature under the ambient atmospheric pressure for 2 hours. After the reaction was completed, the resultant reaction liquid was cooled to room temperature, and a sample of the resultant reaction liquid was dissolved in toluene and subjected to the same gas chromatographic analysis.

and two carbon atoms of the 12 carbon atoms being adjacent to each other and bonded to the oxygen atom.

3. The method of producing a cyclododecanone compound as claimed in claim 1, wherein the epoxycyclododecane compound is selected from the group consisting of epoxycyclododecane, epoxycyclododecenes, epoxycyclododecadienes, and epoxycyclododecatrienes.

4. The method of producing a cyclododecanone compound as claimed in claim 1, wherein the cyclododecanone compound is selected from the group consisting of saturated and unsaturated cycloaliphatic compounds having a cyclic structure formed from 12 carbon atoms and a carbonyl structure formed from an oxygen atom and one of the 12 carbon atoms bonded to the oxygen atom through a double bond.

5. The method of producing a cyclododecanone compound as claimed in claim 1, wherein the cyclododecanone compound is selected from the group consisting of cyclododecanone, cyclododecenones, cyclododecadienones and cyclododecatrienones.

6. The method of producing a cyclododecanone compound as claimed in claim 1, wherein the catalyst is present in an amount of 0.0001 to 0.1 mole per mole of the epoxycyclododecane compound.

7. The method of producing a cyclododecanone compound as claimed in claim 1, wherein the isomerizing reaction for the epoxycyclododecane compound is carried out at a temperature of 100° C. to 300° C.

8. The method of producing a cyclododecanone compound as claimed in claim 1, wherein the inert gas comprises at least one member selected from the group consisting of helium, neon, argon, krypton, xenon, hydrogen, nitrogen, carbon monoxide, carbon dioxide, methane, and ethylene gases.

* * * * *